United States Patent
Mouw

(10) Patent No.: US 9,138,325 B2
(45) Date of Patent: Sep. 22, 2015

(54) LAMINA IMPLANT AND METHOD

(71) Applicant: Globus Medical, Inc., Audubon, PA (US)

(72) Inventor: Graham J. Mouw, Fort Lauderdale, FL (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 13/940,217

(22) Filed: Jul. 11, 2013

(65) Prior Publication Data

US 2014/0018920 A1   Jan. 16, 2014

Related U.S. Application Data

(60) Provisional application No. 61/670,581, filed on Jul. 11, 2012.

(51) Int. Cl.
| | | |
|---|---|---|
| *A61F 2/44* | (2006.01) | |
| *A61B 17/70* | (2006.01) | |
| *A61F 2/28* | (2006.01) | |
| *A61F 2/30* | (2006.01) | |

(52) U.S. Cl.
CPC .............. *A61F 2/44* (2013.01); *A61B 17/7071* (2013.01); *A61F 2002/2835* (2013.01); *A61F 2002/30471* (2013.01); *A61F 2002/30476* (2013.01); *A61F 2002/30538* (2013.01); *A61F 2002/30578* (2013.01); *A61F 2002/4475* (2013.01)

(58) Field of Classification Search
CPC ............. A61B 17/025; A61B 17/1671; A61B 17/7062; A61B 17/7064; A61B 17/7067; A61B 17/7068; A61B 17/7071; A61F 2/444425; A61F 2/4611; A61F 2002/4475; A61F 2002/30601
USPC .............. 623/17.11–17.16; 606/246–249, 279
See application file for complete search history.

(56) References Cited

U.S. PATENT DOCUMENTS

| | | | | |
|---|---|---|---|---|
| 2008/0262623 | A1* | 10/2008 | Bagga et al. ............... | 623/17.16 |
| 2010/0057127 | A1* | 3/2010 | McGuire et al. ............. | 606/246 |
| 2010/0174315 | A1* | 7/2010 | Scodary et al. .............. | 606/248 |
| 2011/0125269 | A1* | 5/2011 | Moskowitz et al. ....... | 623/17.11 |
| 2012/0078303 | A1* | 3/2012 | Malek ........................... | 606/250 |
| 2012/0078304 | A1* | 3/2012 | Jensen et al. ................. | 606/251 |
| 2012/0158060 | A1* | 6/2012 | Abrahams et al. ............ | 606/248 |
| 2012/0165942 | A1* | 6/2012 | Khanna ...................... | 623/17.16 |
| 2013/0060283 | A1* | 3/2013 | Suh et al. ...................... | 606/246 |
| 2013/0197641 | A1* | 8/2013 | Shepard et al. ............. | 623/17.11 |

OTHER PUBLICATIONS

Patel et al. "Histologic Evaluation of High Speed Burr Shavings Collected During Spinal Decompression Surgery". Orthopedics. 1; 32.*
Patel et al. "Histologic Evaluation of High Speed Burr Shavings Collected During Spinal Decompression Surgery". Orthopedics. 1;32.*

* cited by examiner

Primary Examiner — Eduardo C Robert
Assistant Examiner — Michelle C Eckman

(57) ABSTRACT

A prosthetic implant for restoring lamina after a laminectomy. The implant is generally a lamina-sized construct having a hollow interior. The lamina removed during the laminectomy may be converted to autologous bone that may then be placed inside the hollow interior of the implant. The implant may then be secured to the spine at the site of the laminectomy so that lamina restoration can occur as the hollow interior of the implant solidifies with bone growth.

18 Claims, 6 Drawing Sheets

US 9,138,325 B2

LAMINA IMPLANT AND METHOD

CROSS-REFERENCES TO RELATED APPLICATIONS

This patent application claims the benefit of U.S. Provisional Patent Application Ser. No. 61/670,581 filed Jul. 11, 2012, which application is incorporated herein by this reference thereto.

BACKGROUND OF THE INVENTION

1. Field of the Invention

This invention relates to the field of lamina replacement.

2. Description of the Related Art

Laminectomies, removal of the spinal lamina, are the most common surgical procedures in spinal surgery. Laminectomies are routinely performed in the cervical and lumbar spine to allow decompression of key areas of the spine.

Cervical laminectomies allow decompression of the spinal cord and nerve roots. Patients may present with a radiculopathy (pain in the arms), myelopathy (weakness in arms and legs), or a combination of both. Cervical laminectomies are performed over multiple cervical levels and are an effective technique for cervical decompression and relief of symptoms. Removal of the posterior spinal elements, the cervical lamina, predisposes the patient to develop spinal instability, deformity, and pain. The posterior spinal elements, lamina, allow posterior structural support for the spine and an attachment for the posterior neck muscles. Some surgeons will perform a spinal fusion after cervical laminectomy to prevent spinal deformity. Cervical fusion creates an unnatural state for the neck, however, as the entire fused neck segment is non-mobile. There is a high risk of adjacent level segment instability after cervical fusion since all of the force with motion is transferred to the segment above and below the fusion.

Cervical laminoplasty has been devised for decompression and reconstruction of the cervical lamina, but has certain limitations that have decreased its usefulness in spinal surgery. The primary issue is the technical difficulty of cervical laminoplasty. A "trough" needs to be drilled on one side of the junction of the lamina and lateral mass. This is a technically challenging technique. After a complete trough is formed on one side of the lamina-lateral mass junction, a partial trough is then formed on the opposite side. The lamina is then lifted off the dura and a wedge of bone is secured between the lifted-up side of the lamina Therefore, current cervical laminoplasty techniques allow adequate decompression of only one side of the spinal cord and nerve roots.

Lumbar laminectomies are performed for decompression of the cauda equina and nerve roots. As a large laminectomy defect is created, however, spinal instability can occur. There can also be additional scar formation, as the muscle has to rest directly on the dura after a traditional laminectomy. Some surgeons use hemilaminotomies, where only a portion of the lamina is removed to decompress the nerve roots. However, hemilaminotomies are technically difficult, time consuming, and cannot adequately decompress the bilateral nerve roots and central dura. Lumbar fusions are routinely performed after lumbar laminectomies, but represent a plethora of technical difficulties and predispose the patient to "adjacent level" instability as forces are displaced above or below the fusion. A fusion also involves the placement of large pedicle screws through the pedicle of the vertebral body. Misplacement of the screws has resulted in cerebrospinal fluid (CSF) leaks, nerve injury, and paralysis.

As such, there is still a need for a prosthetic implant for restoring the lamina after laminectomies while providing complete relief for the patient.

SUMMARY OF THE INVENTION

The present invention is directed towards a prosthetic implant for restoring lamina after a laminectomy. The implant is generally a lamina-sized construct having a hollow interior. The lamina removed during the laminectomy may be converted to autologous bone that may then be placed inside the hollow interior of the implant. The implant is then secured to the remaining portion of the spine at the site of the laminectomy. An attaching agent, such as one or more plates with screws, may be used to secure the implant to the spine. Over time, the autologous bone inside the hollow interior of the implant will solidify as bone grows through the interior of the implant.

DESCRIPTION OF THE PREFERRED EMBODIMENTS

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. It is to be understood, however, that the same or equivalent functions, features, and sequences may be accomplished by different embodiments that are also intended to be encompassed within the spirit and scope of the invention.

Figure 1:
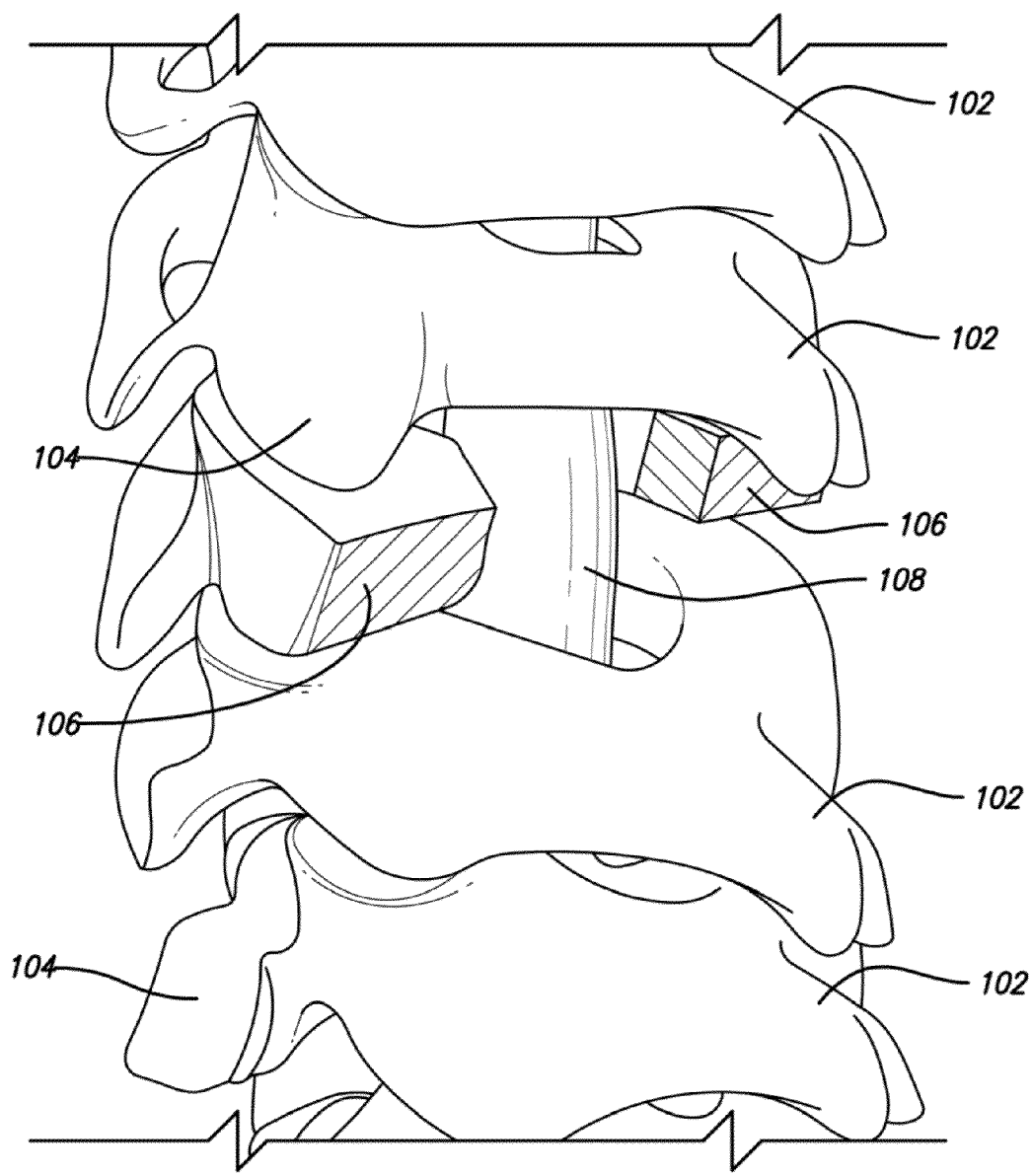
FIG. 1 shows a perspective view of the spine with the lamina removed.

The present invention represents a novel implant and technique for the restoration of the lamina after cervical decompression or lumbar decompression. As seen in FIG. 1, when a surgeon performs a cervical or lumbar laminectomy by removing the lamina 102 of a spine 100, a gap is formed. In one embodiment of the present invention, an appropriately sized lamina replacement implant 200 may then be selected for attachment to the spine 100 on each side 106 of the gap.

Figure 2A:
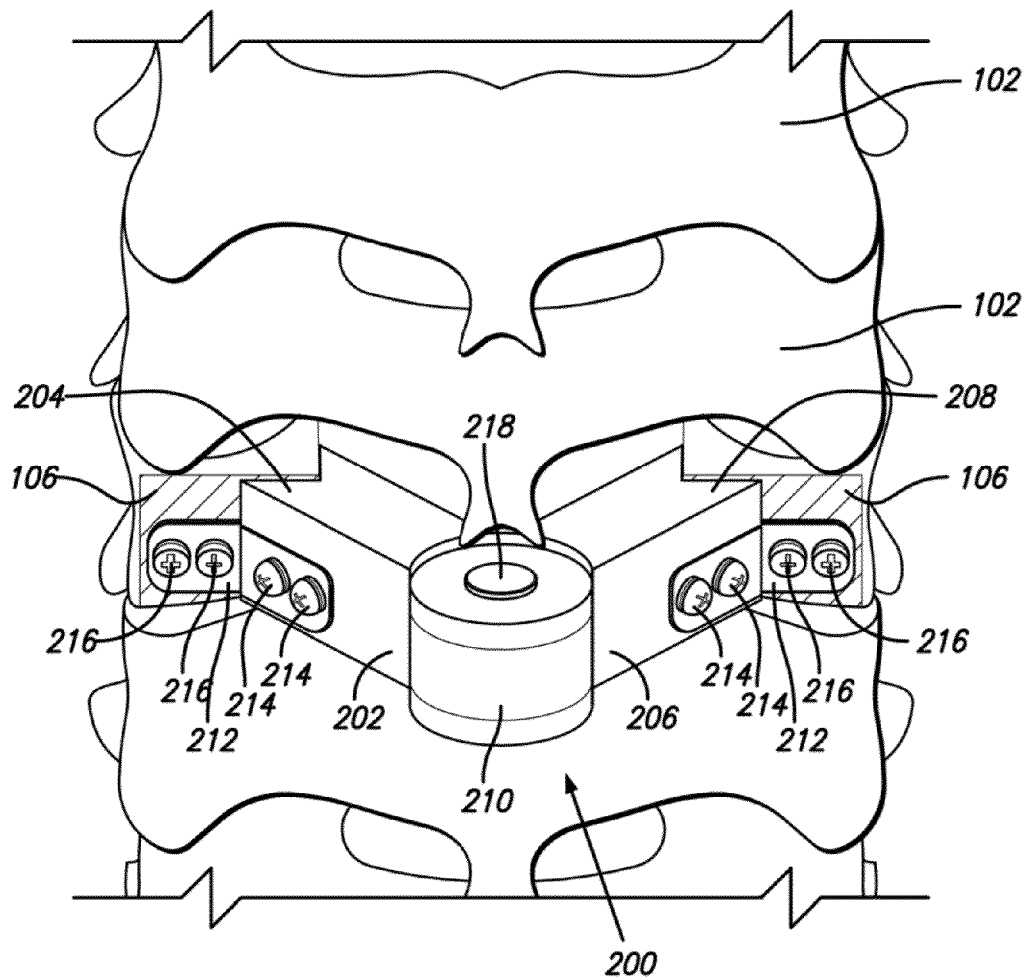
FIG. 2A shows a rear view of the cervical region of the spine with the lamina removed with an embodiment of the present invention in place.
Figure 2B:
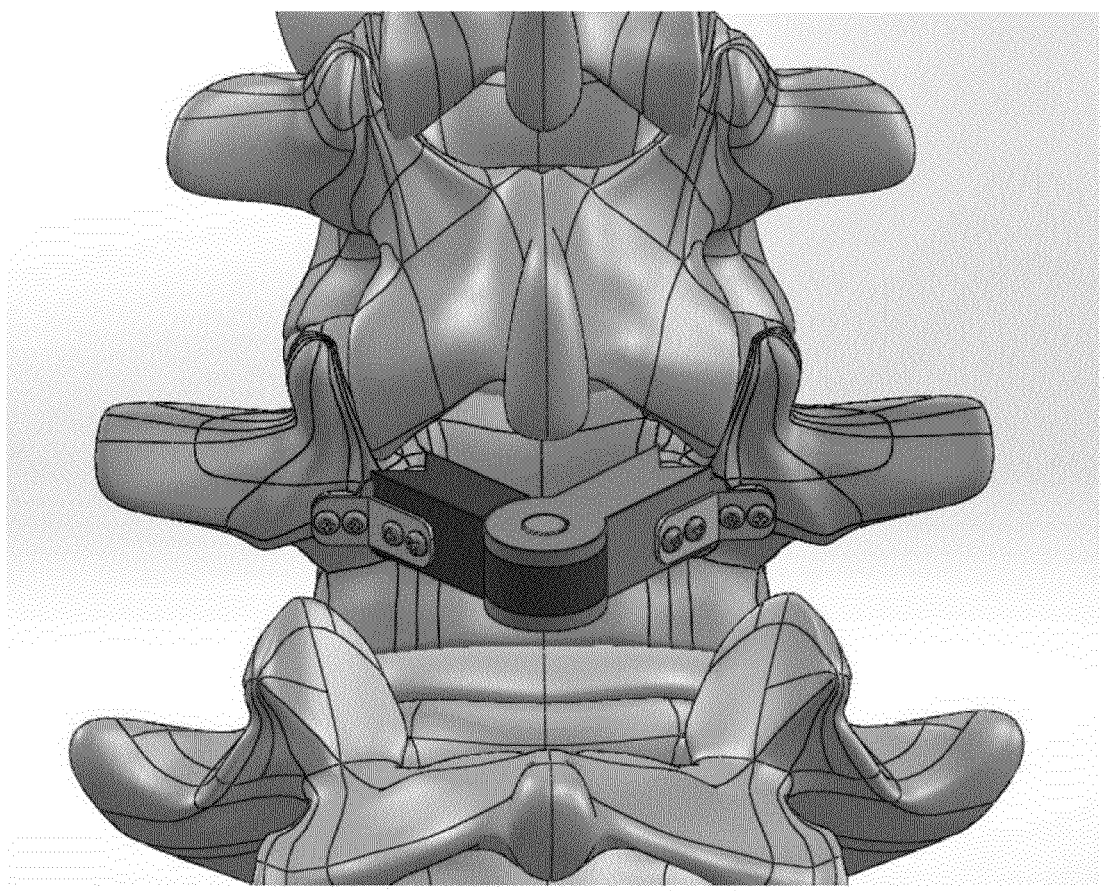
FIG. 2B shows a rear view of the lumbar region of the spine with the lamina removed with an embodiment of the present invention in place.

This embodiment of the present invention, therefore, includes a lamina replacement implant 200. As shown in FIG. 2A and FIG. 2B, it may be secured to the spine 100 at the site of the removed lamina. The implant 200 is shaped in a way that allows attachment to the spine 100 while providing support for the spine 100 and/or protection for the spinal cord 108. In a preferred embodiment, the implant 200 has a hollow body having a first arm 202 terminating at a first end 204, a second arm 206 terminating at a second end 208, connected together in a mid-section 210. The hollow body may be made of PEEK (polyether ether ketone) or other suitable biocompatible material.

Figure 3:
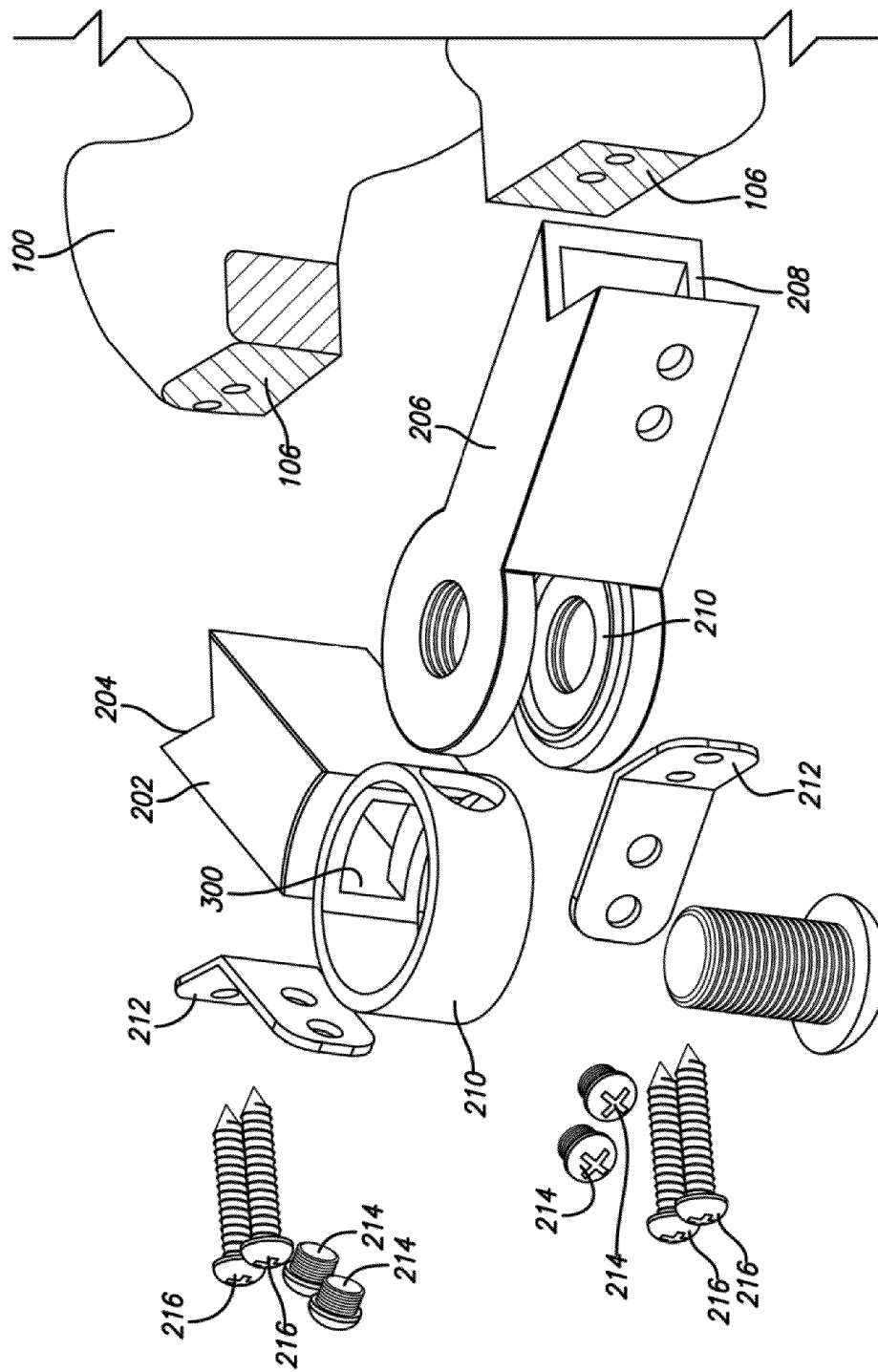
FIG. 3 shows a perspective view of an embodiment of the present invention with its parts separated and the attachment sites of the spine.

In the embodiment in FIG. 3, the body of the implant 200 has a first arm 202 and a second arm 206, with the first arm 202 and the second arm 206 connected to form the midsection 210. In this embodiment, the first arm 202 and second arm 206 are connected in a movable way to allow for adjustments to their orientation. Examples include the use of hinges, pivots, joints, or telescoping features. This allows the implant 200 to be adjusted to fit many of the different sizes of the spine 100 at different spinal levels. Accordingly, one such implant 200 could be adjusted outwardly to fit the largest lumbar spinal level or inwardly to fit a much smaller cervical spinal level so that it may be applicable to many or all of the spinal levels. Alternatively, a larger two-arm implant 200 could be fashioned to fit just the lumbar spinal levels and a smaller two-arm implant could be fashioned to fit just all or a portion of the cervical spinal levels. Once the adjustment has been made such that the ends of the two arms satisfactorily mate with the spine 100, this particular orientation can be locked in place by a locking mechanism 218, such as a screw, pin, glue, or any equivalents. The locking mechanism may be made of titanium, solidified bone graft material, or other biocompatible material. The two arms would mate with the lateral mass in the cervical spine and facet/pedicle in the lumbar spine.

In another embodiment, the body of the implant 200 is one piece or even multiple pieces but without a defined hinge or pivot portion. Such an implant 200 could have several mounting holes or slots so as to be able to mount to a range of spinal levels of several different sizes. Alternatively, such an embodiment could involve two flexible arms 202, 206 or a flexible mid-section 210. The flexible portion could be elastic such that it tends to spring back to a neutral shape until it is fixed to the spine 100. Yet a further alternative would be that the flexible portion could be designed to readily plastically deform so that there is no significant tendency of the implant 200 to return to a neutral shape once flexed.

Figure 4:
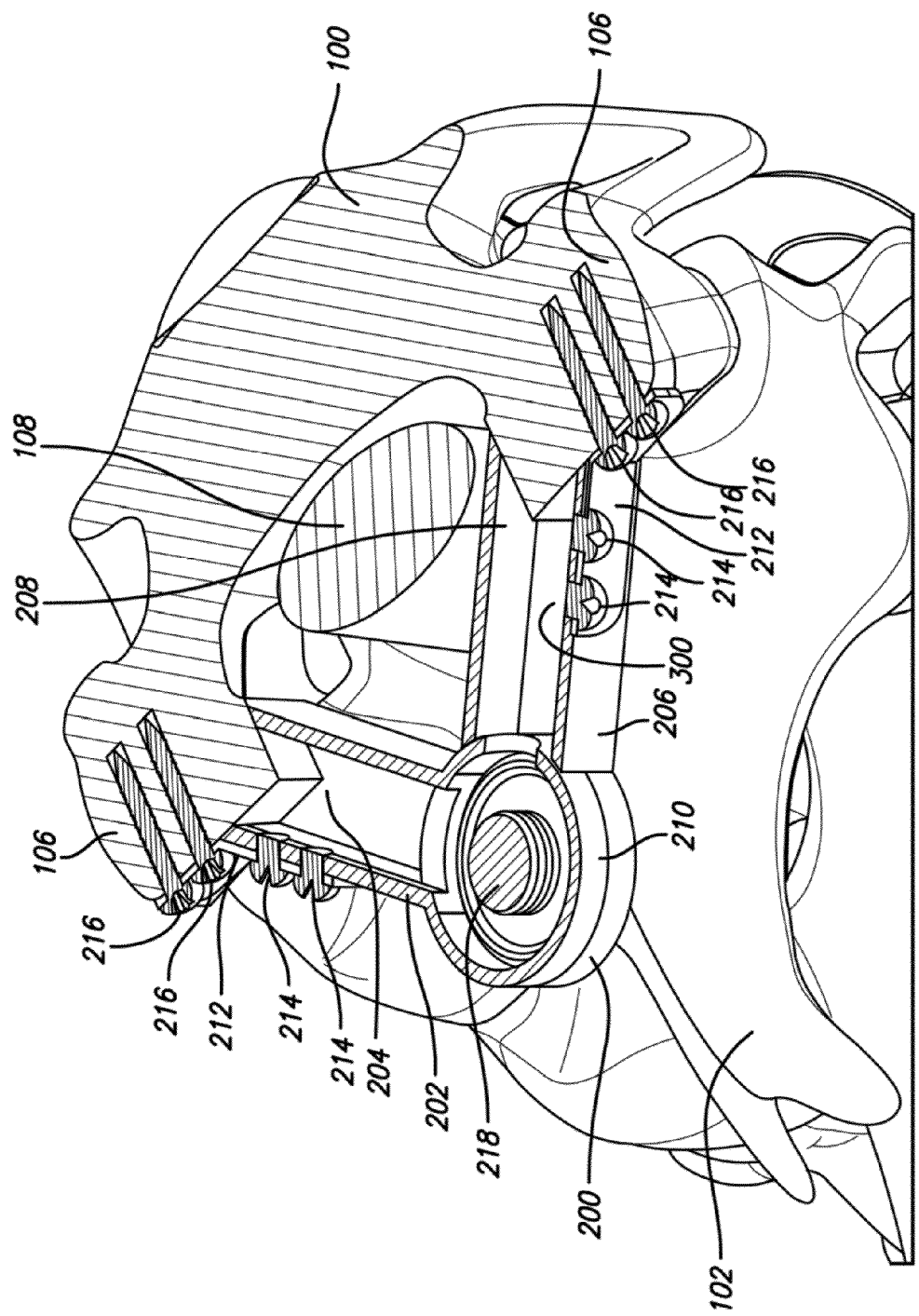
FIG. 4 show a cross-sectional perspective view of an embodiment of the present invention secured to the spine.
Figure 5:
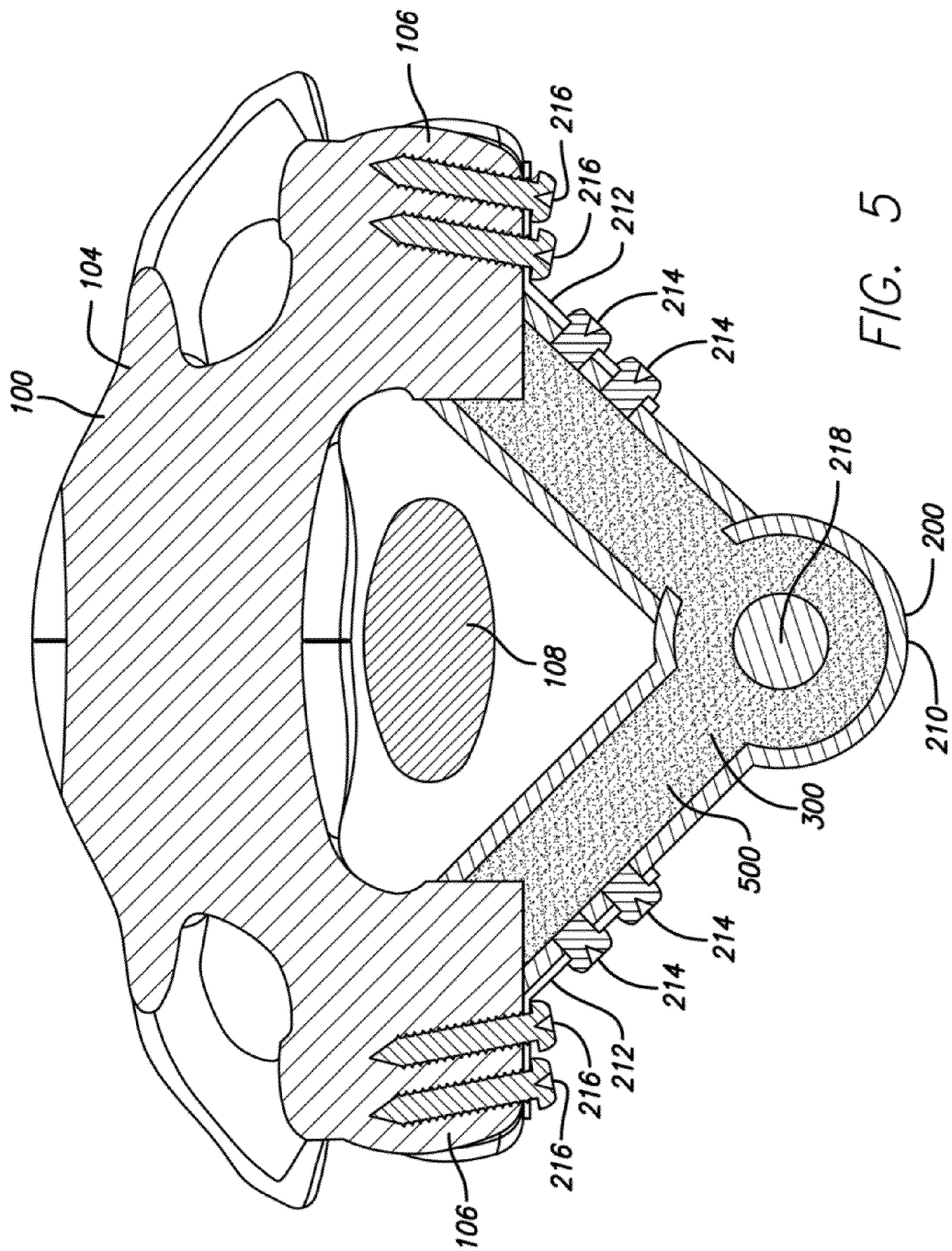
FIG. 5 shows a cross-sectional isometric top view of an embodiment of the present invention secured to the spine after bone growth.

Once the surgeon adjusts the implant 200 and moves it into place, such as in FIGS. 2, 4 and 5, the surgeon may secure the implant 200 to the spine 100. This can be done by several different securing means. In the embodiment shown in FIG. 4, the implant 200 is secured to the spine 100 using plates, braces, or brackets fixed to the implant 200 and/or the spine 100 by screws 214, 216. Implant screws 214 of appropriate length may attach the plates 212 to the arms 202, 206 of the implant 200, and spinal screws 216 of appropriate length may attach the plate 212 to the spine 100. In one preferred embodiment, the lengths are approximately 6 mm-8 mm for the cervical region and approximately 12 mm-14 mm for the lumbar region. In another embodiment, the plates 212 and screws 214, 216 may comprise titanium or a titanium alloy for their biocompatible properties. In other embodiments, the securing means may instead be a malleable strap, a biodegradable material, or a durable or biodegradable adhesive.

The implant 200 should be attached so as to allow contact between the remaining portions of the exposed spine 100 and a region on or in the implant 200 that comprises a bone graft region 300 that can facilitate bone growth through the implant 200. In one embodiment, at least a portion of the implant 200 may be hollow. These hollow portions 300 can be fitted securely so any bone graft material 500 will not leak out. In a preferred embodiment, the first and second ends of the arms also comprise bevels to allow the implant to more securely attach to the spine. When that midsection is adjusted, the angle of the bevels may change orientation as well. Because of this, in some embodiments, the mating faces of the arms may also be adjustable, malleable, or realignable so that the bevels are at a correct orientation to securely attach to the lateral mass 106 for ease of mating and alignment with the spine and to better ensure a tight fit therebetween. To further facilitate securement to the spine 100, the first and second ends may further comprise one or more notches into which remaining portions of the spine are contoured, fitted or wedged. One or more additional buffers, such as linings, gap-filling adhesives, mating gaskets, or cushioning, may be added to prevent any leakages of bone graft material 500 from the secured implant 200 or to better fit and secure the implant to the spine 100. The spine and/or the ends of the arms may be further shaped to each other's contours to form a more secure attachment. The inclusion of adjustable mating facings further reduces the time and effort required in contouring, fitting, or wedging the implant or spine.

Thus, in one embodiment, a hollow interior 300 of the implant 200 may be filled with bone graft material 500 that is intended to solidify through the implant. As shown in FIG. 5, the bone graft material 500 may become as strong as bone and provide additional strength for the implant 200. In one embodiment, after a spinal laminectomy, the removed portions of lamina may be crushed into autologous bone (autograft) and used as bone graft material 500 in the implant 200. This would aid the implant 200 to solidify over time as bone continues to grow through the implant 200. Such autologous bone graft material 500 may also decrease the chances that such material will be rejected by the patient's body. Indeed, PEEK implants in spinal surgery, filled with autograft and fitted in the disc space, have shown to produce robust bone growth through the interior where autograft has been placed. As PEEK has modules of elasticity that resemble that of bone, it may be a preferential template for lamina replacement, although other compositions may be used and new compositions are sure to prove useful with advancements in the field.

Alternatively, the bone graft material 500 could be composed of autograft material from other portions of the body, allograft material from the bones of other people (such as cadavers, donors, or stem cell cultures), xenograft material from animals, synthetic replacements, other similar substitutes, or a combination thereof. In one embodiment, the implant uses larger bone pieces or fragments or other bone graft material that may have been pre-solidified or partially solidified before it is implanted into a patient.

In one embodiment, as shown in FIG. 5, the surgeon may drill into the exposed sections of the spine 100 and fill the void created thereby with bone graft material 500 that is also used to fill adjacent hollow portions 300 of the implant 200 so that new bone formed inside the ends of the implant and the new bone formed inside the drilled void within the adjacent spine can form together, allowing for a more secure bone attachment. The embodiment in FIG. 5 shows a drilled area with rounded edges, but other shapes may be used for stronger securement or greater surface areas. In one embodiment, a drill with a hollow center is used so the drilled area has a peg in the middle for greater surface area to promote bone growth. In another embodiment, several holes are drilled in each lateral mass 106 for increased surface area. Alternatively, the implant 200 may include a solid end mass that approximately mates with the interior surface of the void created in the spine 100 and design with a surface material and/or texture that facilitates bone growth or solidification, such surfaces may include nanostructured regions, including nanotextured and nanoporous regions. The solid end mass may also be a solid nub used for anchoring the implant in the bone. This solid nub can be made from titanium, bone made from bone graft material, or other biocompatible material.

Additionally, the implant portions themselves may be composed of biodegradable materials so that the bone graft material 500 solidifies with the spine 100 and the biodegradable implant later biodegrades ultimately to restore the spinal lamina 102.

While the present invention has been described with regards to particular embodiments and some of their equivalents, it is recognized that additional variations of the present invention with their functionally equivalent features may be devised without departing from the inventive concept.

What is claimed is:

1. A method for lamina replacement and restoration, comprising:
   a. performing a laminectomy to remove a portion of a lamina of a spine;
   b. converting the lamina into autologous bone;
   c. filling an implant having a hollow interior with the autologous bone, the implant having a first arm, a second arm and a hinge, the first arm and the second arm movably engaged to each other through the hinge;
   d. adjusting the hinge so that one or more ends of the implant may be positioned before being secured to a spine;
   e. locking the hinge to lock the orientation of the first arm relative to the second arm; and
   f. securing the implant to a spine at a site of the laminectomy
   wherein the hollow interior of the implant extends from the hinge to a distal end of the first arm and distal end of the second arm.

2. The method of claim 1, wherein the implant is open at areas of contact with the spine so the autologous bone touches the spine.

3. The method of claim 2, further comprising shaping the spine or implant to fit each other at areas of contact.

4. The method of claim 1, wherein the implant is adjustable in shape or size, and further comprising a step of adjusting the shape or size of the implant to fit at the site of the laminectomy.

5. A method for lamina replacement and restoration, comprising:
   a. filling an implant having a hollow first arm, a hollow second arm and a hollow hinge with bone graft material;
   b. adjusting a distance between distal ends of the implant using the hinge before securing the implant to the spine; and
   c. securing the implant to the spine at a site where lamina has been removed
   wherein the hollow interior of the implant extends from the hinge to a distal end of the first arm and distal end of the second arm.

6. The method of claim 5, wherein the implant is open at areas of contact with the spine so the bone graft material touches the spine.

7. The method of claim 6, further comprising a step of shaping the spine and the implant to each other at areas of contact.

8. The method of claim 6, wherein the bone graft material is autologous bone.

9. The method of claim 6, wherein the bone graft material is allograft bone, xenograft bone, or synthetic material.

10. The method of claim 5, wherein the implant is adjustable in shape or size, and further comprising a step of adjusting the implant to fit the spine.

11. The method of claim 10, further comprising locking the implant after adjustment of size or shape.

12. A prosthetic for a spine, comprising a hollow implant and a securing mechanism to secure the implant to surfaces of a spine where lamina has been removed, the implant further comprising first and second ends and a hinge therebetween, wherein the hinge is configured to allow the implant to form an angle that is adjustable so that the first and second ends of the implant can reach said surfaces,
   wherein the hinge is locked to lock the orientation of the first end with respect to the second end
   wherein the hollow interior of the implant extends from the hinge to a distal end of the first end and distal end of the second end.

13. The prosthetic of claim 12, wherein the implant has a hollow interior filled with bone graft material.

14. The prosthetic of claim 13, wherein the bone graft material is made from autologous bone.

15. The prosthetic of claim 13, wherein the bone graft material is made from allograft bone, xenograft bone, or synthetic material.

16. The prosthetic of claim 13, wherein the implant is open at one or both ends and configured to place the bone graft materials in contact with the spine.

17. The prosthetic of claim 16, wherein one or both ends of the implant are shaped to fit to the surfaces of the spine at the areas of contact.

18. The prosthetic of claim 13, wherein the implant is adjustable in shape or size to fit different spinal levels.

* * * * *